(12) United States Patent
Funabasama et al.

(10) Patent No.: US 10,593,022 B2
(45) Date of Patent: Mar. 17, 2020

(54) MEDICAL IMAGE PROCESSING APPARATUS AND MEDICAL IMAGE DIAGNOSTIC APPARATUS

(71) Applicant: TOSHIBA MEDICAL SYSTEMS CORPORATION, Otawara-Shi (JP)

(72) Inventors: Shintaro Funabasama, Utsunomiya (JP); Yasuko Fujisawa, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/496,440

(22) Filed: Apr. 25, 2017

(65) Prior Publication Data

US 2017/0323432 A1 Nov. 9, 2017

(30) Foreign Application Priority Data

Apr. 26, 2016 (JP) ................................. 2016-087957
Apr. 21, 2017 (JP) ................................. 2017-084123

(51) Int. Cl.
*G06T 5/00* (2006.01)
*A61B 6/00* (2006.01)
(Continued)

(52) U.S. Cl.
CPC .............. *G06T 5/005* (2013.01); *A61B 6/032* (2013.01); *A61B 6/463* (2013.01); *A61B 6/486* (2013.01);
(Continued)

(58) Field of Classification Search
CPC ......... A61B 8/0833; A61B 5/055; A61B 8/06; A61B 2576/023; A61B 5/0044;
(Continued)

(56) References Cited

U.S. PATENT DOCUMENTS

| 6,292,683 B1* | 9/2001 | Gupta | A61B 5/055 324/307 |
| 2007/0127809 A1* | 6/2007 | Leach | G06T 7/0016 382/154 |

(Continued)

FOREIGN PATENT DOCUMENTS

| JP | 2003-210456 A | 7/2003 |
| JP | 2012-239796 A | 12/2012 |
| JP | 2013-192912 A | 9/2013 |

*Primary Examiner* — Jingge Wu
(74) *Attorney, Agent, or Firm* — Oblon, McClelland, Maier & Neustadt, L.L.P.

(57) ABSTRACT

In one embodiment, a medical image processing apparatus which analyzes blood flow dynamics in a predetermined region of a subject, the blood flow dynamics being generated from medical images obtained by imaging the predetermined region in time sequence over a plurality of time phases. The medical image processing apparatus includes memory circuitry configured to store a program; and processing circuitry configured to correct pixel values of a second medical image according to an amount of deformation of the second medical image when the second medical image is aligned with a first medical image by executing the program read out from the memory circuitry, the first medical image and the second medical image being among the medical images in the plurality of time phases.

16 Claims, 13 Drawing Sheets

(51) Int. Cl.
  *G06T 7/33*   (2017.01)
  *A61B 6/03*   (2006.01)
  *G06T 5/50*   (2006.01)
  *G06T 7/00*   (2017.01)
  *G06T 11/60*  (2006.01)

(52) U.S. Cl.
  CPC ............ *A61B 6/507* (2013.01); *A61B 6/5217* (2013.01); *A61B 6/5235* (2013.01); *G06T 5/50* (2013.01); *G06T 7/0016* (2013.01); *G06T 7/337* (2017.01); *A61B 6/50* (2013.01); *A61B 6/541* (2013.01); *G06T 11/60* (2013.01); *G06T 2207/10081* (2013.01); *G06T 2207/20221* (2013.01); *G06T 2207/30061* (2013.01); *G06T 2207/30104* (2013.01)

(58) Field of Classification Search
  CPC ....... A61B 6/503; A61B 6/504; A61B 8/0891; A61B 8/483; A61B 8/5223; G06T 2207/10016; G06T 2207/10132; G06T 2200/04; G06T 2207/20104; G06T 2207/10116; G06T 2207/20021; G06T 2207/30101; G06T 7/20; G06T 5/005
  See application file for complete search history.

(56) References Cited

U.S. PATENT DOCUMENTS

| | | | |
|---|---|---|---|
| 2008/0095417 A1* | 4/2008 | Pedrizzetti | A61B 8/0883 382/128 |
| 2008/0247622 A1* | 10/2008 | Aylward | A61B 90/36 382/131 |
| 2009/0116715 A1* | 5/2009 | Bredno | A61B 6/481 382/130 |
| 2011/0054295 A1* | 3/2011 | Masumoto | A61B 5/055 600/407 |
| 2011/0103665 A1* | 5/2011 | Gulsun | G06T 7/248 382/131 |
| 2011/0144495 A1* | 6/2011 | Wilkening | A61B 8/0883 600/443 |
| 2011/0305405 A1* | 12/2011 | Kawamura | G06T 7/003 382/294 |
| 2012/0070059 A1* | 3/2012 | Furukawa | A61B 3/102 382/131 |
| 2012/0201441 A1* | 8/2012 | De Oliveira | G01R 33/56509 382/131 |
| 2012/0300904 A1 | 11/2012 | Shimada et al. | |
| 2013/0261445 A1* | 10/2013 | Ertel | A61B 5/0044 600/431 |
| 2014/0037168 A1* | 2/2014 | Ishikawa | A61B 5/055 382/130 |
| 2015/0005659 A1 | 1/2015 | Masumoto | |
| 2015/0154756 A1* | 6/2015 | Gerganov | G06T 7/32 382/131 |
| 2015/0161790 A1* | 6/2015 | Takahashi | A61B 5/0245 600/424 |
| 2015/0245776 A1* | 9/2015 | Hirohata | A61B 6/032 600/504 |
| 2015/0327780 A1* | 11/2015 | Kano | A61B 5/0261 600/407 |
| 2016/0098836 A1* | 4/2016 | Yamato | A61B 6/50 382/128 |
| 2016/0117797 A1* | 4/2016 | Li | G06T 3/0081 382/128 |
| 2016/0253800 A1* | 9/2016 | Gurevich | A61B 5/0071 382/128 |
| 2016/0343134 A1* | 11/2016 | Averkiou | G06T 7/0016 |
| 2017/0071479 A1* | 3/2017 | Kano | A61B 5/02007 |
| 2018/0042565 A1* | 2/2018 | Wilson | A61B 6/482 |

\* cited by examiner

MEDICAL IMAGE PROCESSING APPARATUS AND MEDICAL IMAGE DIAGNOSTIC APPARATUS

CROSS-REFERENCE TO RELATED APPLICATION

This application is based upon and claims the benefit of priority from Japanese Patent Application No. 2016-087957, filed on Apr. 26, 2016, and Japanese Patent Application No. 2017-084123, filed on Apr. 21, 2017, the entire contents of all of which are incorporated herein by reference.

FIELD

An embodiment of the present invention relates to a medical image processing apparatus and a medical image diagnostic apparatus.

BACKGROUND

In dynamic contrast imaging, a process in which a contrast medium administered to a subject flows into an organ or tissue to be diagnosed and flows out of the organ or tissue is imaged over plural time phases. Pixel values of medical images acquired by dynamic imaging over plural time phases reflect changes in a level of the contrast medium in the blood. A time density curve (TDC), which is a graphic plot of successive changes in the pixel values, allows a level of a tissue lesion, such as a degree of malignancy to be determined. Also, by analyzing the TDC, it is possible to learn a half life of the contrast medium in the blood, a blood flow rate, and a blood volume, and thereby qualitatively and quantitatively evaluate the blood flow. In this way, various diseases are diagnosed based on results of blood flow dynamics analysis conducted using medical images obtained by dynamic imaging. With such dynamic imaging, positional displacement occurs due to breathing of the subject during the imaging, posing a problem in conducting image analysis.

For example, dynamic imaging in a lung field involves holding breath a few times. The lungs are organs whose volumes change greatly with each breath. It is difficult for the subject to inflate the lungs in a same way each time imaging is performed. Because images are acquired by performing imaging by holding breath a few times, the volumes and shapes of the lungs in the acquired images may vary each time. In such a case, a conventional technique aligns plural images differing from one another in time phase and conducts blood flow dynamics analysis based on the aligned images using a time density curve.

DETAILED DESCRIPTION

A medical image processing apparatus according to an embodiment will be described below with reference to the drawings.

In one embodiment, a medical image processing apparatus which analyzes blood flow dynamics in a predetermined region of a subject, the blood flow dynamics being generated from medical images obtained by imaging the predetermined region in time sequence over a plurality of time phases. The medical image processing apparatus comprising: memory circuitry configured to store a program; and processing circuitry configured to correct pixel values of a second medical image according to an amount of deformation of the second medical image when the second medical image is aligned with a first medical image by executing the program read out from the memory circuitry, the first medical image and the second medical image being among the medical images in the plurality of time phases.

(1) Configuration

Figure 1:
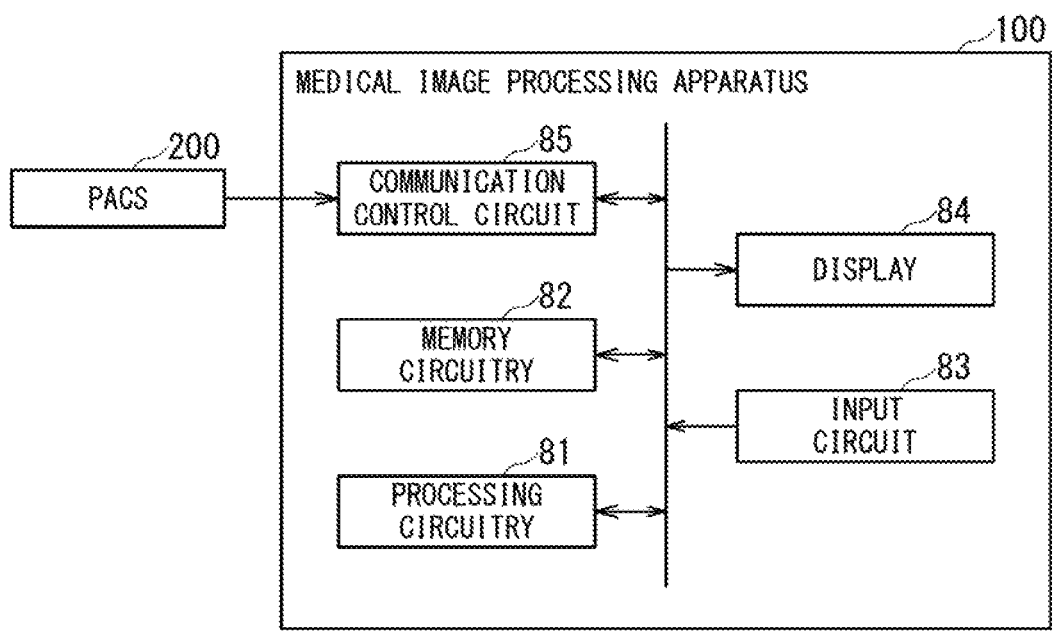
FIG. 1 is a conceptual configuration diagram showing an example of the medical image processing apparatus according to the embodiment.

FIG. 1 is a conceptual configuration diagram showing an example of the medical image processing apparatus according to the embodiment. As shown in FIG. 1, the medical image processing apparatus 100 is configured based on a computer, and is ready to intercommunicate with external apparatus via a network such as a LAN (Local Area Network). The medical image processing apparatus 100 is made up of basic hardware including processing circuitry 81, memory circuitry 82, an input circuit 83, and a display 84. The medical image processing apparatus 100 is connected to picture archiving and communication systems (PACS) 200 through a communication control circuit 85 via an electronic network.

The communication control circuit 85 implements various communication protocols according to network topologies. The electronic network as referred to herein means an entire information network using telecommunications technology and includes a hospital backbone LAN, a wireless/wired LAN, the Internet, a telephone communication network, an optical fiber communication network, a cable communication network, and a satellite communication network. The medical image processing apparatus 100 acquires image data of medical images from the PACS 200 via the electronic network.

Note that the PACS 200 and medical image processing apparatus 100 may be built as systems in the cloud.

The processing circuitry 81 may be configured of a special-purpose hardware or be configured to implement various types of functions by software processing of its built-in processor. As an example here, a description will be given of a case where the processing circuitry 81 implements various types of functions by software processing of its processor.

The above-described term "processor" means, e.g., a circuit such as a special-purpose or general-purpose CPU, a special-purpose or general-purpose graphics processing unit (GPU), an application specific integrated circuit (ASIC), a programmable logic device, and a field programmable gate array (FPGA). The above-described programmable logic device includes, e.g., a simple programmable logic device (SPLD) and a complex programmable logic device (CPLD). The processing circuitry 81 implements various types of functions by reading out programs stored in the memory circuit 82 and executing the programs. Additionally or alternatively, the processing circuitry 81 implements various types of functions by reading out programs stored in its own processer and executing the programs.

Further, the processing circuitry 81 may be configured of a single processor or may be configured of a combination of plural processors which are independent of each other. In the latter case, plural memory circuits 82 may be provided for the respective processors so that programs executed by each processor are stored in the memory circuit 82 corresponding to this processor. As a further modification, one memory circuit 82 may collectively store all the programs corresponding to the respective functions of the plural processors.

The memory circuit 82 is configured of, e.g. a hard disc, an optical disc, and a semiconductor memory element such as a RAM (Random Access Memory) and a flash memory. The memory circuit 82 may be configured as a circuit to which a portable medium such as a USB (Universal Serial Bus) memory and a DVD (Digital Video Disk) is detachably connected. The memory circuit 82 stores image data and data necessary for executing programs in addition to various types of programs executed by the processing circuitry 81 (including an application program and an operating system). Additionally, the memory circuit 82 may store a program of a GUI (Graphical User Interface) which enables input of various types of commands for controlling the operating system from the input circuit 83.

The input circuit 83 is a circuit configured to output a signal which is inputted from an input device such as a pointing device. As an example here, the input device is assumed to be included in the input circuit 83. When the input device is operated by an operator, the input circuit 83 generates an input signal depending on this operation and outputs this input signal to the processing circuitry 81.

The display 84 is a display device such as a liquid crystal display panel, a plasma display panel, and an organic EL (Electro Luminescence) panel. The display 84 displays an image under the control of the processing circuitry 81.

Figure 2:
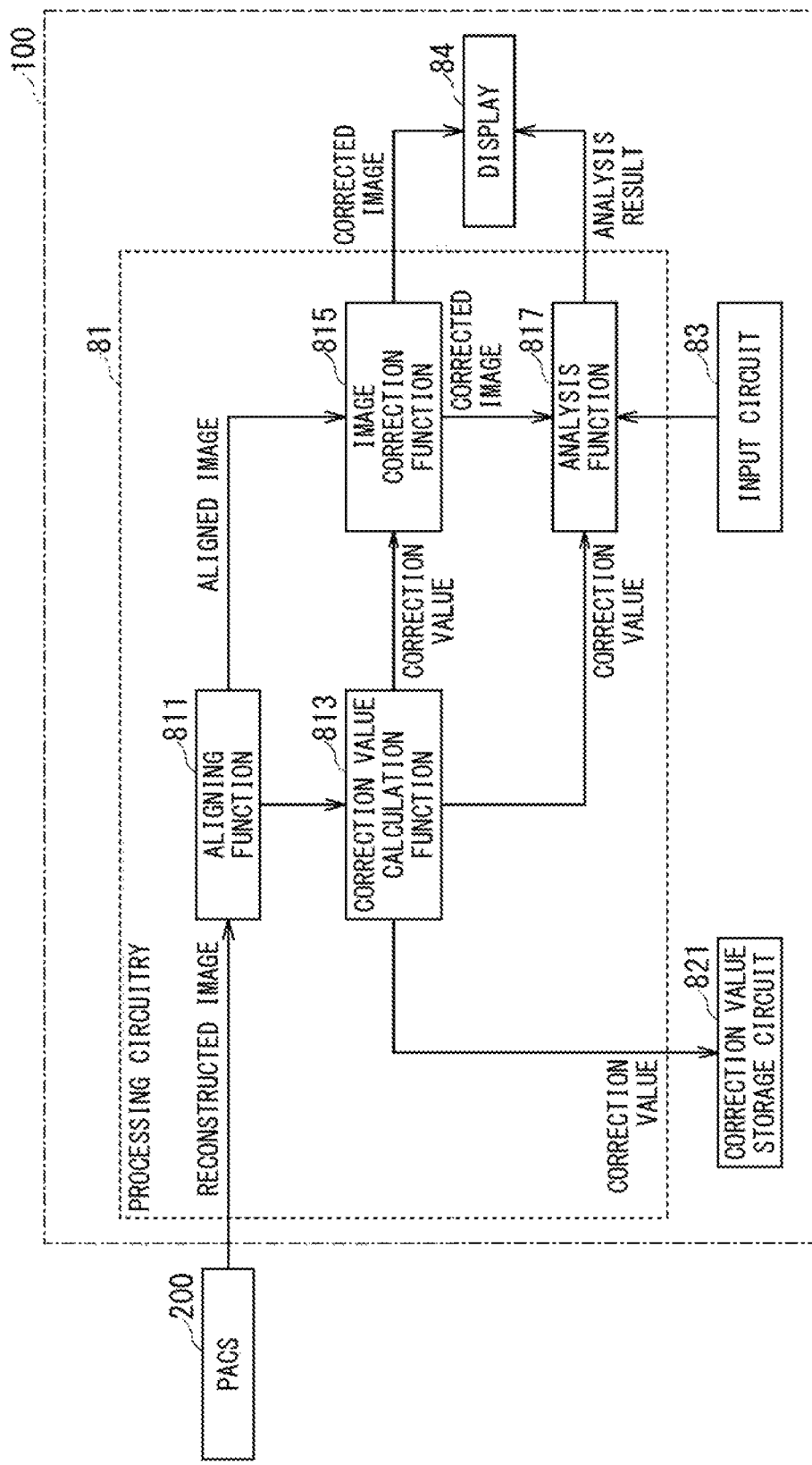
FIG. 2 is a functional block diagram showing a functional configuration example of the medical image processing apparatus according to the embodiment.

FIG. 2 is a functional block diagram showing a functional configuration example of the medical image processing apparatus 100 according to the embodiment. The medical image processing apparatus 100 includes an aligning function 811, a correction value calculation function 813, an image correction function 815, and an analysis function 817. A correction value memory circuit 821 may be configured as a storage area in the memory circuitry 82 or may be made up of memory circuitry different from the memory circuitry 82.

The processing circuitry 81 includes the aligning function 811, the correction value calculation function 813, the image correction function 815, and the analysis function 817. The aligning function 811, correction value calculation function 813, image correction function 815, and analysis function 817 are implemented when the processing circuitry 81 executes a program stored in the memory circuitry 82.

The aligning function 811 aligns medical images acquired by dynamic imaging over plural time phases. The alignment performed by the aligning function 811 is non-linear alignment or non-rigid alignment. The non-linear alignment or non-rigid alignment, which aligns position with an image serving as a reference, deforms images to be aligned. Hereinafter, the image serving as a reference in alignment will be referred to as a "reference image" and the image to be aligned will be referred to as a "target image".

The correction value calculation function 813 calculates a deformation rate which represents how much the target image has deformed from the reference image as a result of the alignment performed by the aligning function 811. Based on the calculated deformation rate, the correction value calculation function 813 calculates a correction value for use to correct pixel values of the target image. Methods for calculating the deformation rate and correction value will be described later.

The image correction function 815 corrects the pixel values of the target image based on the correction value calculated by the correction value calculation function 813.

Based on the corrected pixel values of the target image, the analysis function 817 creates a time density curve (TDC) and conducts various image analyses including a blood flow dynamics analysis which is based on the TDC. Also, the analysis function 817 creates display data for an alert display which is based on the deformation rate. The image analyses and alert display will be described later.

The correction value memory circuit 821 stores the correction value calculated by the correction value calculation function 813. Also, the correction value memory circuit 821 stores a relational expression between the deformation rate and a pixel value change rate. The relational expression between the deformation rate and the pixel value change rate will be described later.

First, description will be given of a problem of positional displacement of a subject during dynamic imaging due to breathing or body movements. The description will be given by taking as an example case in which medical images are acquired by dynamic imaging on an X-ray CT (computed, tomography) apparatus over plural time phases.

As described above, in dynamic imaging, since the subject is imaged over plural time phases, the positional displacement of the subject due to breathing or body movements presents a problem. For example, dynamic imaging in a lung field involves holding breath a few times. The lungs are organs in which volumes of air taken in change with each breath. Therefore, when breath-hold imaging is performed multiple times, shapes and volumes of the lungs depicted in acquired images will vary in each time phase. Such variations of the shapes and volumes of the lungs among time phases during breath-hold imaging will be referred to as inconsistency of breath-hold state.

Problems caused by inconsistency of breath-hold state among time phases during breath-hold imaging of the lungs will be described below with reference to FIGS. 3 and 4.

Figure 3:
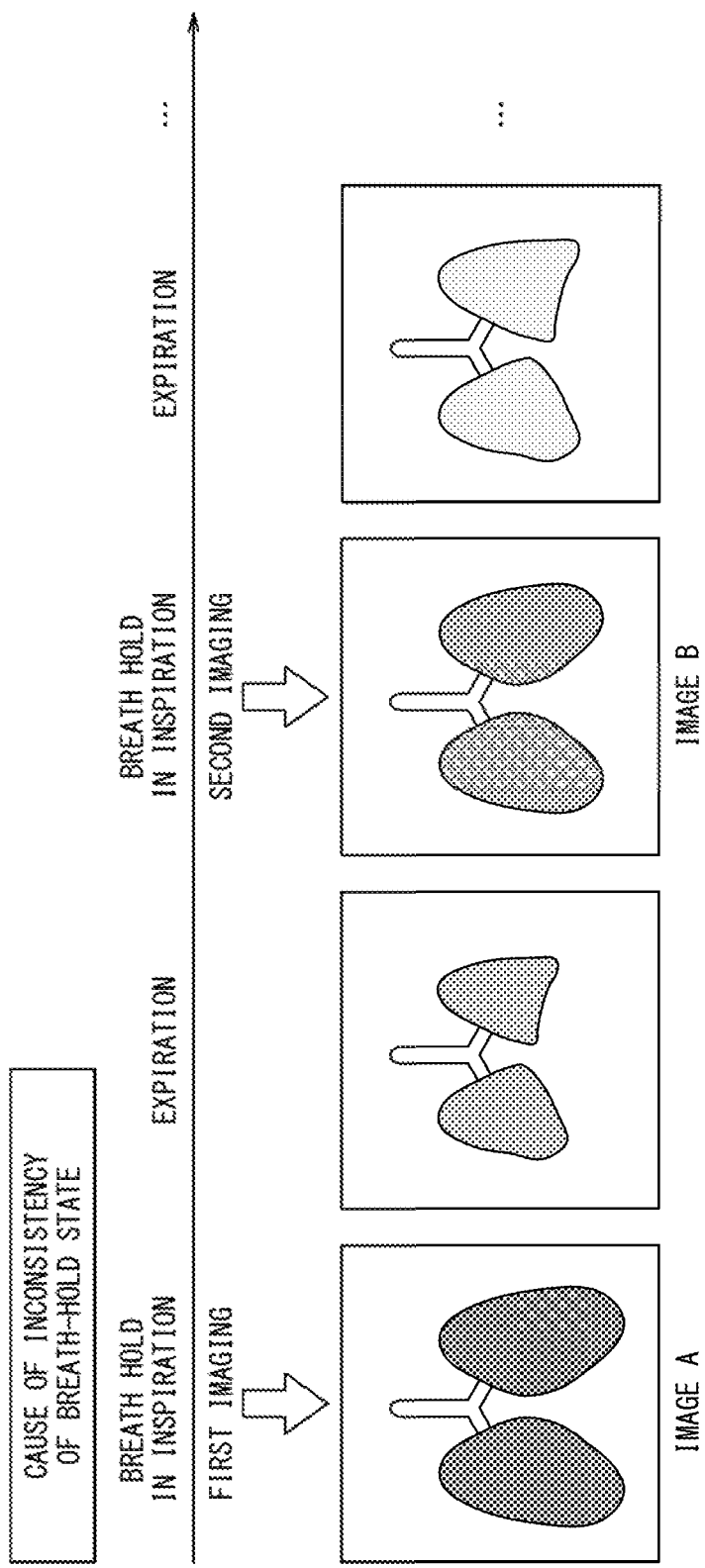
FIG. 3 is a conceptual diagram describing inconsistency of breath-hold state in dynamic imaging of a lung field.

FIG. 3 is a conceptual diagram describing inconsistency of breath-hold state in dynamic imaging of a lung field. In dynamic imaging, imaging is performed multiple times at predetermined intervals, with the subject holding breath. As shown on the left end side of FIG. 3, first imaging is performed in an inhaled state, i.e., with the lungs inflated by breathing in, and consequently image A is generated. After the first imaging, the subject breathes out and freely until the next imaging. In performing second imaging, the subject breathes in again and holds the breath, and imaging is performed in this state, and consequently image B, i.e., the second image from the right in FIG. 3 is generated. In dynamic imaging, imaging is repeated in this way, thereby acquiring lung field images over plural time phases in a breath-hold state during inhalation.

However, it is difficult for the subject to inflate the lungs in a same way every time. As shown in FIG. 3, the lungs are inflated to a smaller extent in image B than in image A even though the two images show the lung field in a breath-hold state. In this way, the shapes and volumes of the lungs vary each time breath-hold imaging is performed.

A TDC is a graph obtained by plotting a CT value of a pixel existing at a same position among plural images differing from one another in time phase and thereby depicting successive CT value changes. Therefore, if there is any positional displacement of the pixel among time phases, it is not possible to create an accurate TDC.

A conventional technique creates a TDC by aligning pixels among plural images differing from one another in time phase using non-linear alignment. However, if the breath-hold state varies among time phases, the volumes of air taken into the lungs vary, affecting the CT value in each image as well.

The CT value has a linear relationship with an X-ray attenuation coefficient of tissue, and a unit of the CT value is HU. Normally, air has an attenuation value of −1000 HU (Hounsfield Unit), water has 0 HU, and hard tissue such as a bone has +1000 HU. A CT image is expressed by gradations ranging from −1000 HU to +1000 HU. That is, differences in densities of substances making up a tissue produce a difference in the X-ray attenuation coefficient, changing the CT value even if the tissue is the same. FIG. 3 shows a case in which the volumes of air taken into the lungs are smaller in image B than in image A. That is, air density in the lung field is smaller in image B than in image A, and consequently the CT value is higher in image B than in image A. Note that in FIG. 3, as an example, the higher the CT value, the lighter the shade on the grayscale.

In this way, if the density of a substance existing in a tissue during imaging varies, the CT value is affected even if the tissue is the same. For example, in the lungs, if the density of air varies among time phases, the CT value becomes higher or lower than actually is. In this way, even if pixel positions are aligned among time phases using non-linear alignment, the CT value is affected by any variation in the density of air actually taken into the lungs. In conducting image analysis among different time phases based on TDCs, more strictly conditions are kept constant, more accurate the analysis is. Even though the shapes of the lungs can be made to coincide among time phases using non-linear alignment, variation in the CT value of each pixel due to inconsistency of breath-hold state cannot be corrected by the non-linear alignment.

Figure 4:
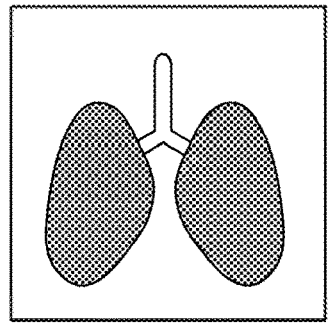
FIG. 4 is a conceptual diagram describing influence of inconsistency of breath-hold state on a time density curve.
Figure 4:
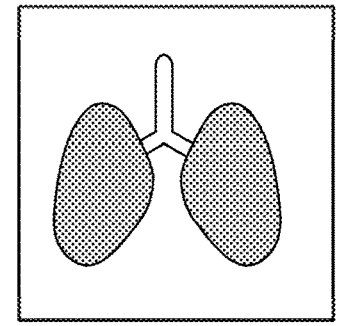
Figure 4:
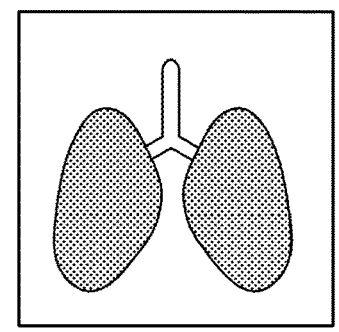
Figure 4:
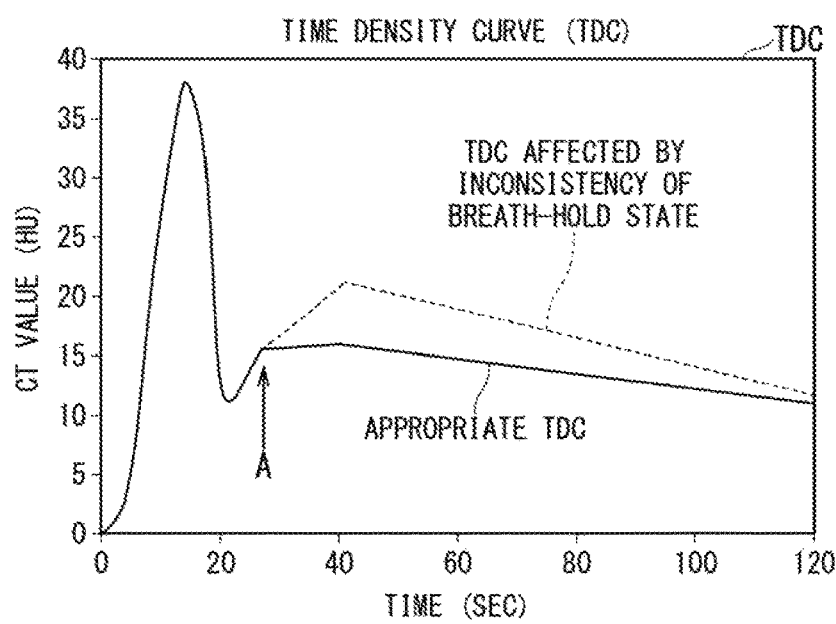

FIG. 4 is a conceptual diagram describing influence of inconsistency of breath-hold state on a time density curve. On the upper left of FIG. 4 is image A acquired by the first imaging in FIG. 3. Similarly, on the upper right of FIG. 4 is image B acquired by the second imaging in FIG. 3. In FIG. 4, description will be given by assuming, as an example, that image A is a reference image serving as a reference in alignment and that image B is a target image to be aligned. Image C in the middle of FIG. 4 is an image obtained by applying non-linear alignment to the target image.

As in the case of FIG. 3, in image B, the volumes of air taken into the lungs are smaller than in image A and the CT value is higher than in image A. Image C obtained by non-linear alignment is a transformation of image B and the CT value of each pixel is the same as image B. That is, whereas image C is identical in shape with image A as a result of non-linear alignment, a condition which affects the CT value of each pixel, i.e., the density of air taken into the lungs, differs from that of image A. In this way, non-linear alignment can match the shapes of the lungs between two images, but cannot match conditions on the CT value of the pixel between the two images.

Therefore, when created using image A and image C, an appropriate TDC cannot be created in some cases as shown in the lower part of FIG. 4. The lower part of FIG. 4 shows TDC graphs, where the abscissa represents an elapsed time from a start of imaging (sec.) while the ordinate represents a CT value (HU). Of the TDCs in the lower part of FIG. 4, the solid line curve is an appropriate TDC. On the other hand, a broken line curve is a TDC affected by inconsistency of breath-hold state. In the lower part of FIG. 4, the TDC affected by inconsistency of breath-hold state deviates from the appropriate TDC after the time indicated by arrow A.

In image C resulting from the non-linear alignment, the CT value of the pixel is larger than in image A because of a smaller amount of air taken in. That is, when image A is used as a reference, the CT value of image C is increased by the influence of the air taken into the lungs. Thus, the medical image processing apparatus 100 according to the present embodiment can correct variation of the CT value, which is caused by differences in the density of air taken into the lung field in a breath-hold state, based on the deformation rate of the target image.

(2) Operation

Operation of the medical image processing apparatus 100 according to the embodiment will be described below in order of step numbers of a flowchart in FIG. 5, by referring to FIGS. 6 to 9 as appropriate.

Figure 5:
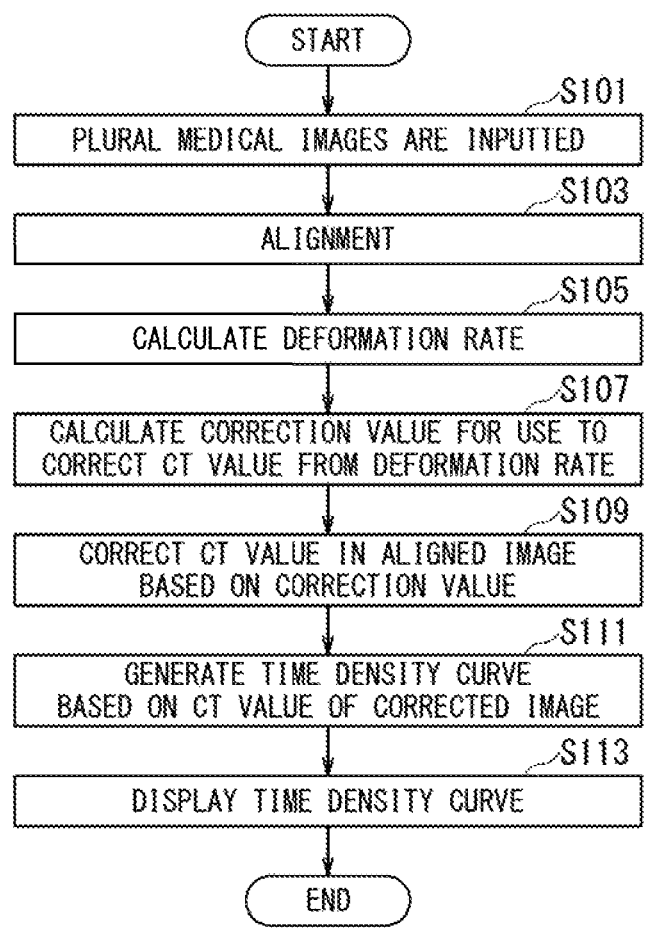
FIG. 5 is a flowchart showing an example of the operation of the medical image processing apparatus according to the embodiment.

FIG. 5 is a flowchart showing an example of the operation of the medical image processing apparatus according to the embodiment.

In step S101, plural medical images are inputted to the medical image processing apparatus 100 from the PACS 200.

In step S103, the aligning function 811 non-linearly aligns the inputted plural medical images. For the non-linear alignment, a grid is set to divide the reference image and target image.

In step S105, the correction value calculation function 813 calculates the deformation rate of the image deformed by the alignment. The deformation rate is calculated from area or volume of the grid set on the reference image and target image.

In step S107, the correction value calculation function 813 calculates a correction value for use to correct the CT value from the deformation rate.

In step S109, using the correction value calculated by the correction value calculation function 813, the image correction function 815 corrects the CT value of the pixel in the CT image resulting from the alignment.

Methods for calculating the deformation rate and correction value of an image will be described below with reference to FIGS. 6 to 8.

Figure 6:
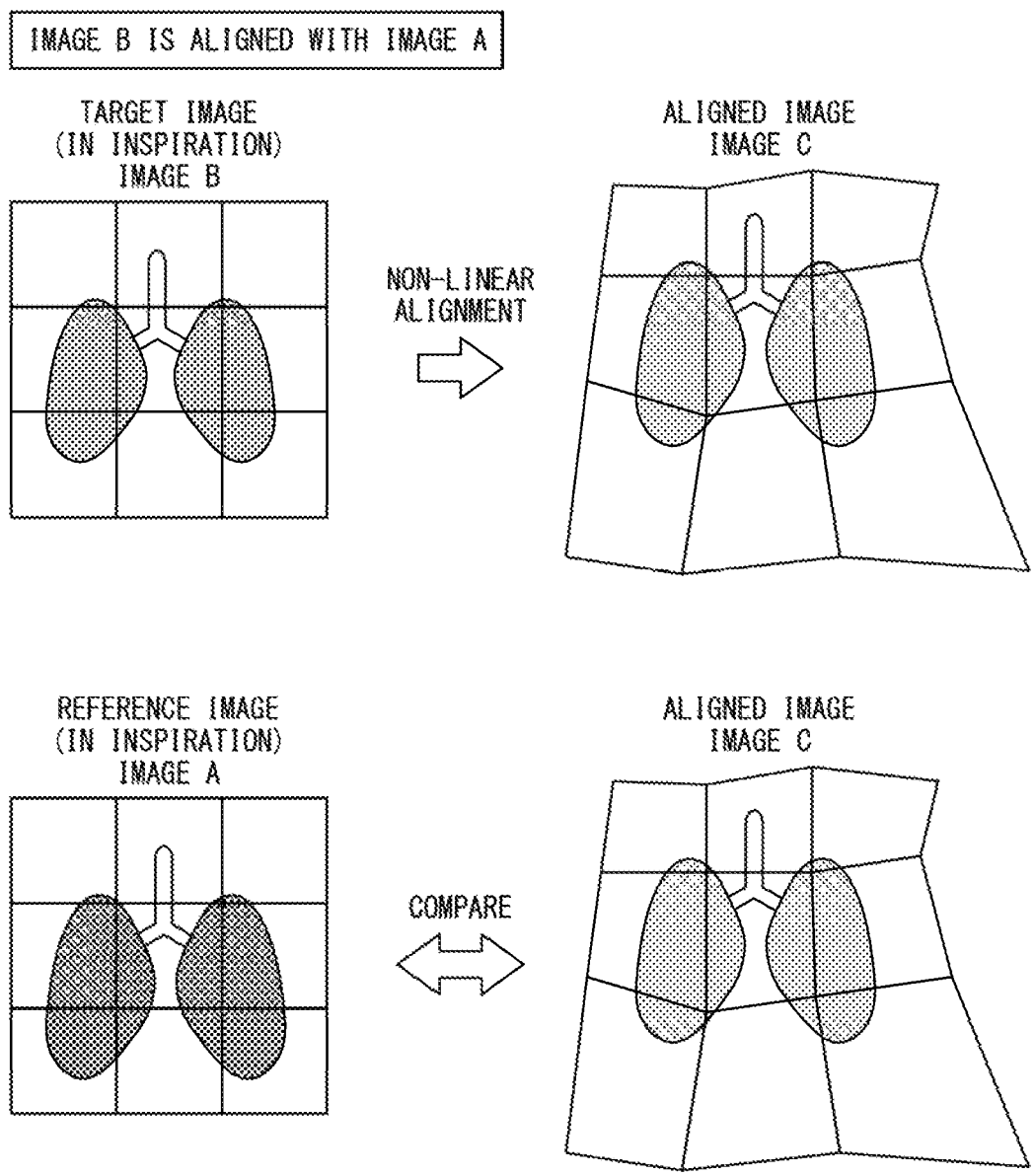
FIG. 6 is a first conceptual diagram describing how to find the deformation rate on the medical image processing apparatus according to the embodiment.

FIG. 6 is a first conceptual diagram describing how to find the deformation rate on the medical image processing apparatus 100 according to the embodiment. FIG. 6 illustrates by way of example how image B is aligned with image A. That is, FIG. 6 shows an example in which image A is a reference image serving as a reference in alignment and image B is a target image to be aligned. Non-linear alignment aligns a target image with a reference image by deforming the target image.

FIG. 6 shows an example in which in order to find an amount of deformation of the target image, a grid is set, dividing the reference image and the target image yet to be deformed. In this way, by applying a same grid to the reference image and the target image yet to be deformed, the amount of deformation of the target image deformed by non-linear alignment can be found from the area of the grid set on the target image.

The upper left part of FIG. 6 shows an example in which a grid is set to divide the target image yet to undergo non-linear alignment. The upper right part of FIG. 6 shows an example of the target image deformed by non-linear alignment. In this way, the grid set before alignment is deformed by non-linear alignment together with the target image.

The lower left part of FIG. 6 shows an example in which a grid is set on the reference image to divide the reference image. The grid set on the reference image is the same as the grid set on the target image yet to undergo non-linear alignment.

On the lower right of FIG. 6, the correction value calculation function 813 compares grid cell areas of same locations of the subject between the target image subjected to the non-linear alignment and the reference image, thereby making it possible to calculate the amount of deformation of the target image in each grid cell caused by the non-linear alignment.

Figure 7:
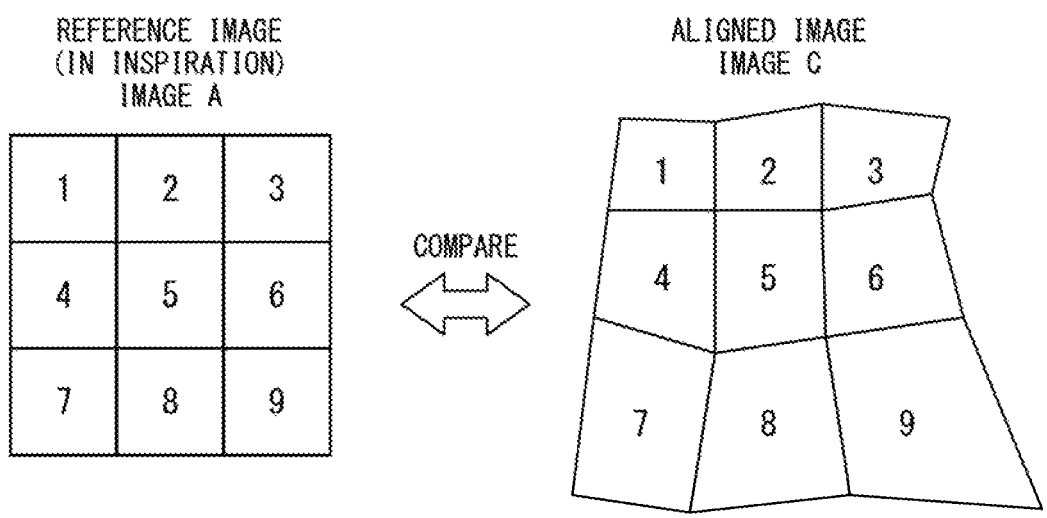
FIG. 7 is a second conceptual diagram describing how to find the deformation rate on the medical image processing apparatus according to the embodiment.

FIG. 7 is a second conceptual diagram describing how to find the deformation rate on the medical image processing apparatus 100 according to the embodiment. The upper right part of FIG. 7 shows how the grid set on the reference image and grid set on the target image described in FIG. 6 have been deformed by non-linear alignment. As described in FIG. 6, the amounts of deformation of the images caused by the non-linear alignment are calculated from the areas of the grids. In the example of FIG. 7, nine grid cells on the target image are assigned same numbers as corresponding ones of nine grid cells on the reference image. The term "corresponding" as referred to herein means, for example, same grid cells or pixels representing same locations of the subject. By finding an area ratio of the target image to the reference image, the deformation rate is calculated. That is, the area of No. 1 grid cell in the target image divided by the area of No. 1 grid cell in the reference image gives the deformation rate.

Using the above method, the deformation rate is calculated for each grid cell. Each grid cell set on the reference image and target image may be equal in size to each pixel of the reference image or may correspond to a region containing plural pixels. Also, for example, when an object is shown in part of the image, the deformation rate may be found using only a region showing the object or using only a region extracted from the image as a sample.

Note that FIGS. 6 and 7 show an example of two-dimensional images for convenience of explanation, but the same is true of three-dimensional images. In the case of three dimensional images, a three-dimensional grid is set and the amounts of deformation and deformation rate are calculated based on a volume of the grid deformed together with the target image as a result of non-linear alignment. Whereas an example of calculating the deformation rate based on deformation of the grid has been described in FIGS. 6 and 7, the deformation rate may be calculated using a vector which represents an amount and direction of travel calculated in relation to non-linear alignment.

The CT value is proportional to the densities of the substances making up a tissue. The shapes of the lungs change with changes in the density of air in the lungs. This makes it possible to correct the CT value by estimating the density of air taken into the tissue based on the changes in the shapes. That is, as shown by Eq. (1), by multiplying the CT value of the target image by a reciprocal of the calculated deformation rate as a correction value, the CT value of the target image can be corrected.

[Mathematical Expression 1]

$$CT \text{ value of corrected image} = CT \text{ value of target image} \times \frac{1}{\text{deformation rate}} \quad (1)$$

In the example described in FIG. 7, the deformation rate is calculated for each grid cell, i.e., for each region containing plural pixels. When one deformation rate is calculated for a region containing plural pixels in this way, the CT value is corrected using the same deformation rate for the plural pixels. When a deformation rate is calculated on a pixel by pixel basis, the CT value is corrected on a pixel by pixel basis. Note that even when a deformation rate is calculated on a pixel by pixel basis, a same deformation rate may be used for correction of a region containing plural pixels. For example, the region containing plural pixels may be corrected using a mean value or a median of the plural pixels. In this way, by correcting plural pixels all together, a correction process can be performed faster than when correction is performed on a pixel by pixel basis.

The CT values may be corrected by calculating the respective deformation rates of the images in all time phases each time imaging is performed or relationships between the deformation rates of images and the rates of change of CT values may be stored in the memory circuitry 82 or the like in advance. For example, by acquiring images in different breath-hold states in advance, the relationships between the deformation rates of images and the rates of change of CT values may be calculated and saved as a graph or look-up table.

Figure 8:
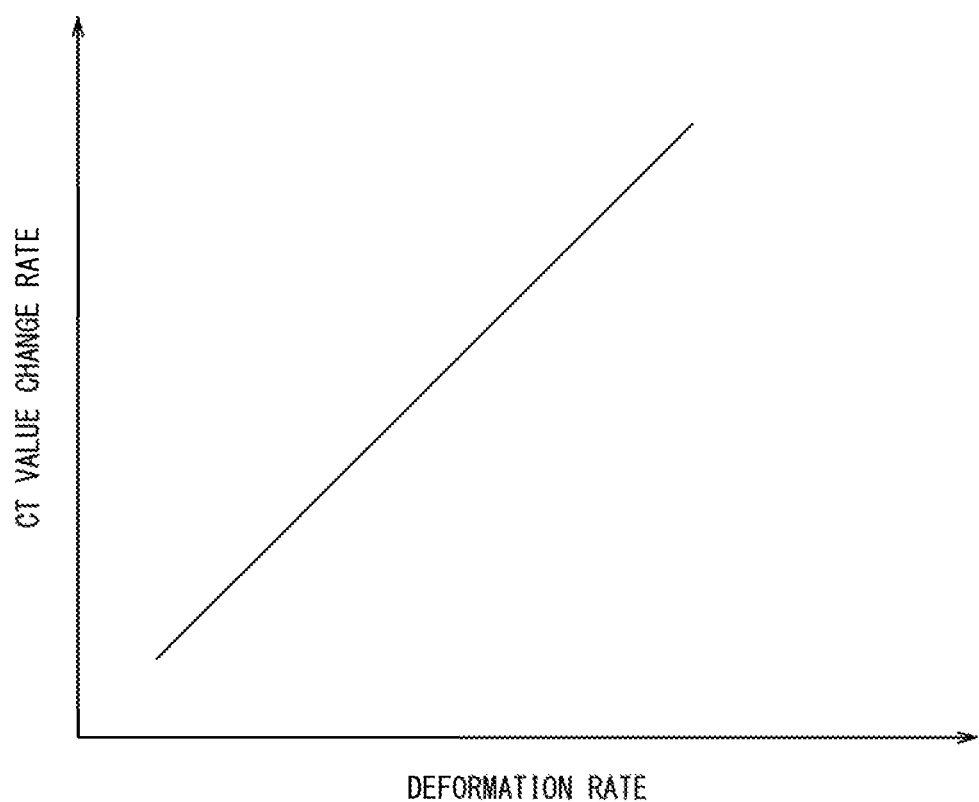
FIG. 8 is a graph showing a relationship between a CT value change rate and image deformation rate calculated by the medical image processing apparatus according to the embodiment.

FIG. 8 is a graph showing a relationship between a CT value change rate and image deformation rate calculated by the medical image processing apparatus 100 according to the embodiment. In FIG. 8, the abscissa represents the image deformation rate while the ordinate represents the CT value change rate. In the example shown in FIG. 8, the image deformation rate and the CT value change rate are in a linear relationship. The relationship between the image deformation rate and CT value change rate is not limited to a linear relationship, and may be expressed by a sigmoid curve or another function.

Also, the relationship between the image deformation rate and CT value change rate may be calculated based on an anatomical structure. For example, the lungs are organs each divided into a few lobes and a relational expression between the image deformation rate and CT value change rate may be found on a lobe by lobe basis and stored in the memory circuitry 82.

Furthermore, the relationship between the image deformation rate and CT value change rate may be calculated based on a posture of the subject during imaging. For example, various imaging postures are available including a supine position, prone position, lateral decubitus position, sitting position, and standing position. A manner in which the lungs are inflated and a manner in which air is taken in vary with the imaging posture. The medical image processing apparatus 100 according to the embodiment may find a relational expression between the image deformation rate and CT value change rate in each imaging posture and store the relational expressions in the memory circuitry 82.

Returning to FIG. 5, the description of the flowchart will be continued.

In step S111, the analysis function 817 generates a time density curve based on the CT value of the corrected image.

In step S113, the display 84 displays the time density curve.

Figure 9:
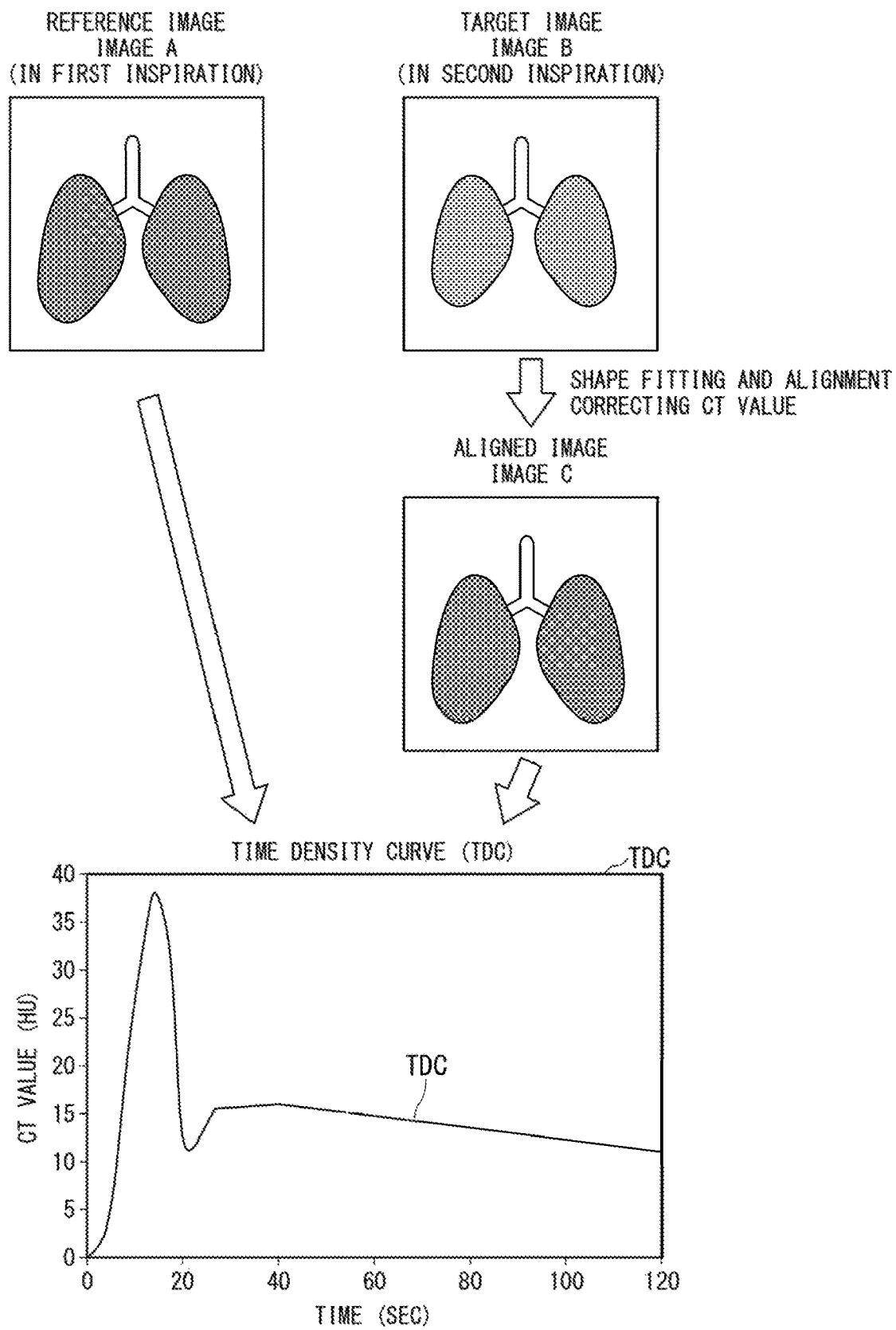
FIG. 9 is a conceptual diagram describing a time density curve which is based on a corrected image on the medical image processing apparatus according to the embodiment.

FIG. 9 is conceptual diagram describing a time density curve which is based on a corrected image on the medical image processing apparatus 100 according to the embodiment. As in the case of FIG. 5, the upper left part of FIG. 9 shows a reference image and the upper right part of FIG. 9 shows a target image. Image C in the middle of FIG. 9 is an image obtained by applying non-linear alignment to the target image and correcting the CT value based on the deformation rate of the image.

As shown by image C in the middle of FIG. 9, application of a correction value based on the deformation rate allows the CT value to be corrected to a same level as image A, i.e., the reference image, on the upper left of FIG. 9. In this way, an appropriate TDC can be created as shown at the bottom of FIG. 9 when created based on a CT image whose CT value has been corrected.

Now that the TDC can be created accurately, precision in determining a lesion level based on the TDC is improved. Also, by analyzing the TDC, it is possible to find a blood flow rate and a blood volume or the like, and to improve precision in calculating these variables as well.

In this way, when the pixel values change as the density of a substance taken into a tissue changes in time sequence, the medical image processing apparatus 100 according to the present embodiment can correct pixel values by estimating the density change of the substance from changes in the shape of the tissue.

Note that whereas a method for correcting the CT value has been described above by taking as an example the lungs, this is not restrictive. For example, the correction method is also applicable to other organs such as the heart, stomach, intestines, and bladder.

Now, a variation which uses the image deformation rate calculated on the medical image processing apparatus 100 according to the present embodiment will be described below with reference to FIGS. 10 to 12.

Figure 10:
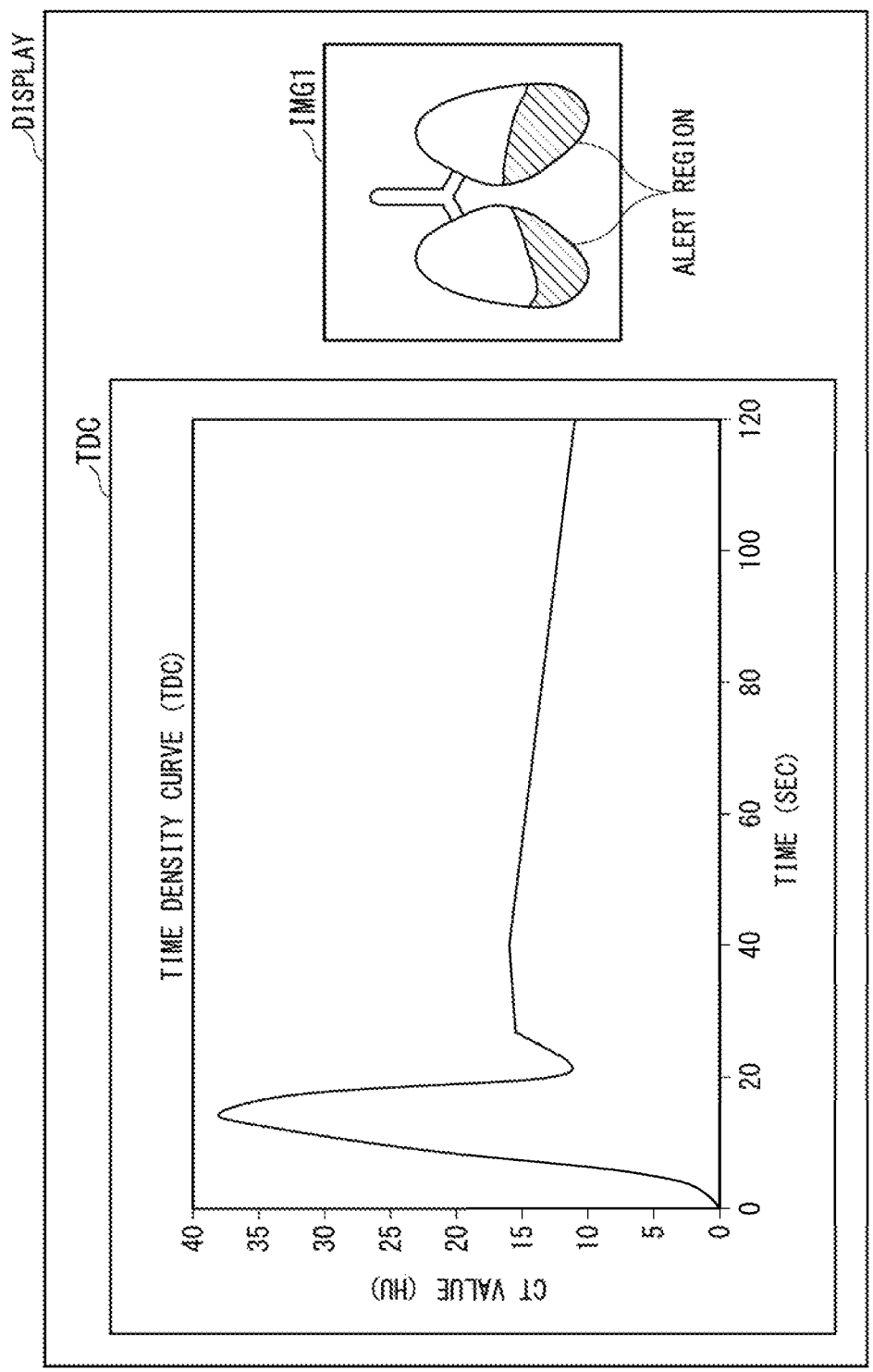
FIG. 10 is a diagram describing a display example of an alert display on the medical image processing apparatus according to the present embodiment.

FIG. 10 is a diagram describing a display example of an alert display on the medical image processing apparatus 100 according to the present embodiment. FIG. 10 shows an example in which a TDC and alert display IMG1 are presented on the display 84. The alert display IMG1 is image made up of an image of the lung field on which an alert region is superimposed. The alert region is a region in which the image deformation rate is higher than a certain threshold. It is conceivable that a region with a high image deformation rate will produce a lower-reliability TDC than a region with a low image deformation rate. That is, a high image deformation rate means a large amount of CT value correction. Therefore, by presenting a region needing such a large amount of correction to a user as an alert region, it is possible to prompt the user to conduct a comprehensive diagnosis taking into consideration not only TDCs but also actual images.

Figure 11:
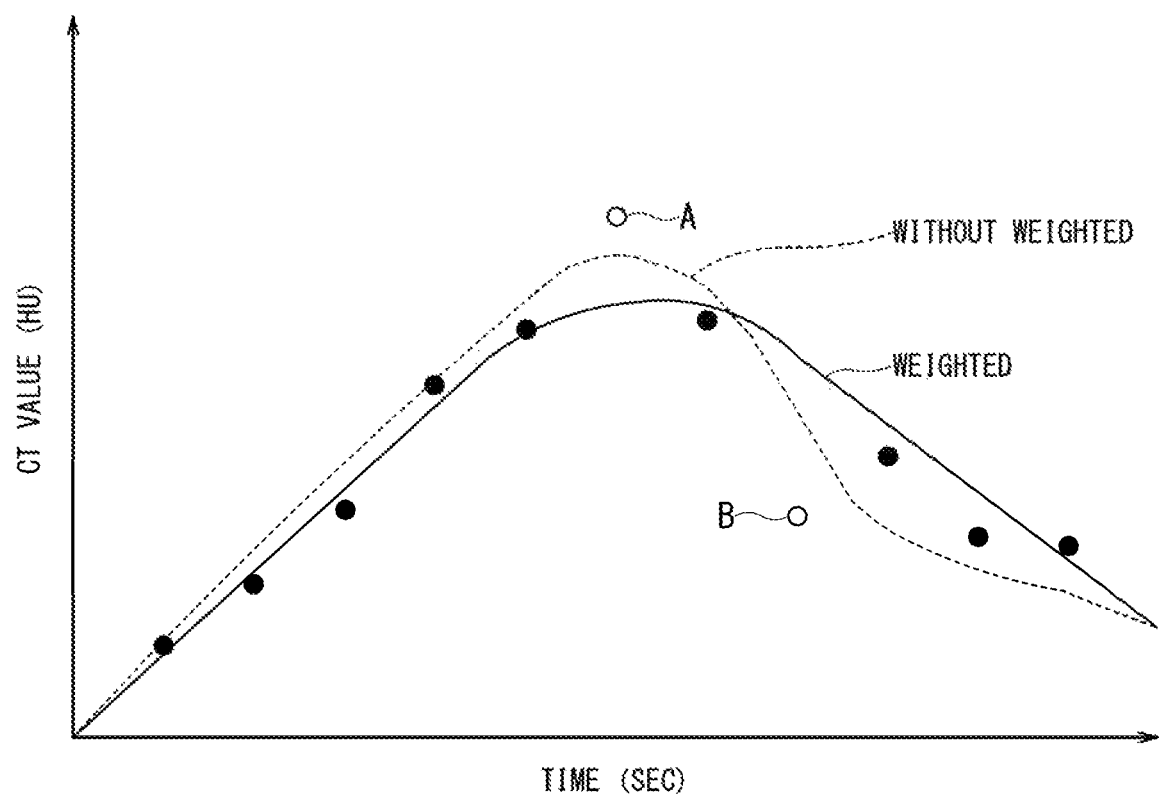
FIG. 11 is a conceptual diagram describing how to create a time density curve by application of a weighted non-linear least squares method based on the image deformation rate on the medical image processing apparatus according to the present embodiment.

FIG. 11 is a conceptual diagram describing how to create a time density curve by application of a weighted non-linear least squares method based on the image deformation rate on the medical image processing apparatus 100 according to the present embodiment. FIG. 11 is a graph obtained by plotting the CT value in each time phase, where the abscissa represents time while the ordinate represents the CT value. Weighting based on the image deformation rate makes it possible to create a curve by reducing effects of CT values having low reliability.

Specifically, the TDC is created by approximating points which represent CT values in different time phases with a curve Point A and point B shown in FIG. 11 have a tendency deviating from a tendency exhibited by other data. For example, point A and point B represent data affected greatly by the above-mentioned inconsistency of breath-hold state and having low reliability. As can be seen, the broken line graph in FIG. 11 is affected greatly by point A and point B.

If a TDC is created using a weighted least squares method based on the amounts of deformation of images, effects of such low-reliability data can be minimized. That is, in curve approximation, weighting based on the image deformation rate can reduce the effects of low-reliability data. The solid line graph in FIG. 11 is a graph created by application of a weighted least squares method which weights point A and point B to a lesser degree than other points. Effects of point A and point B having low reliability are minimized compared to the graph created without application of the weighted least squares method and shown by a broken line in FIG. 11.

Figure 12:
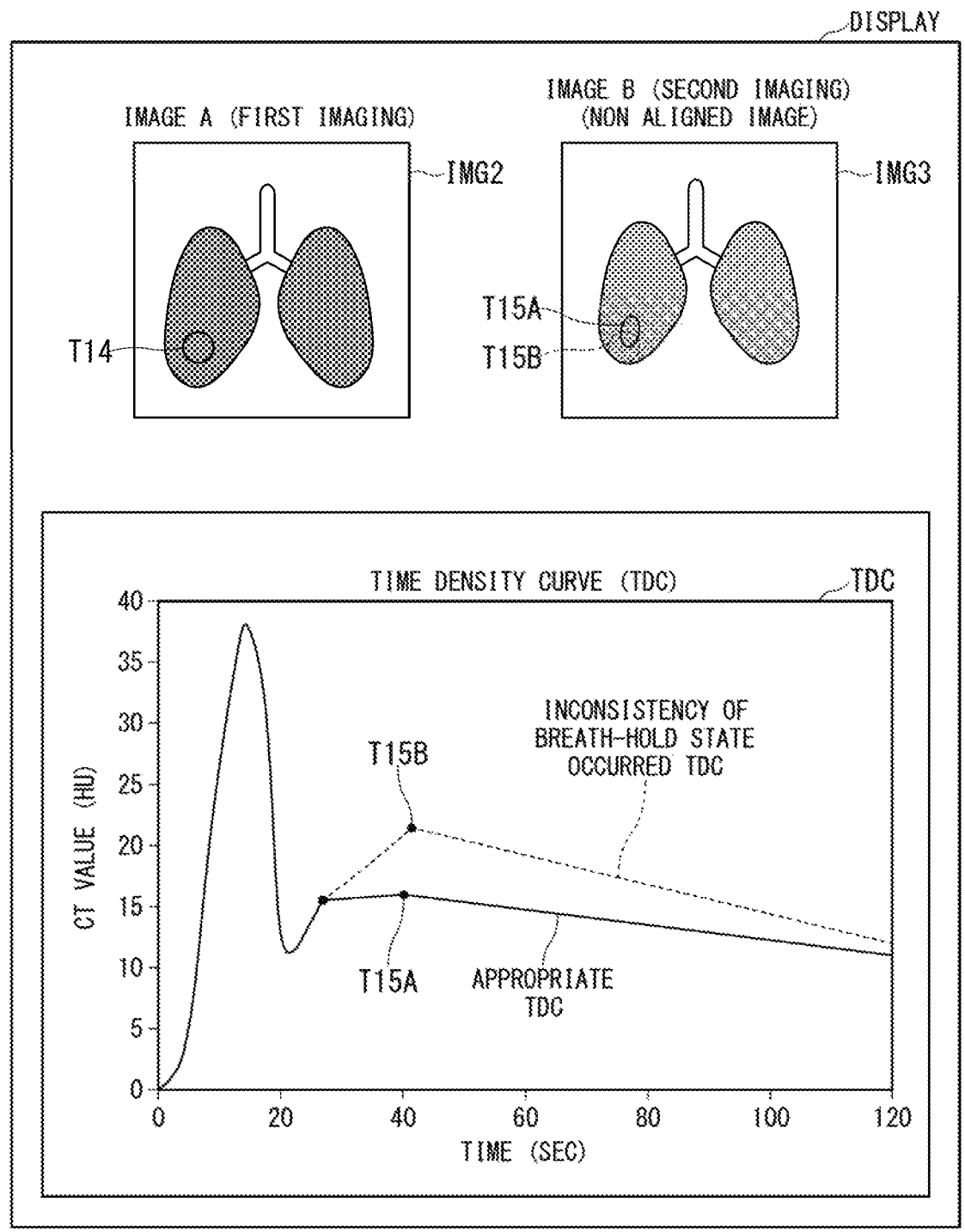
FIG. 12 is a diagram describing tracking display of a region of interest on the medical image processing apparatus according to the embodiment.

FIG. 12 is a diagram describing tracking display of a region of interest on the medical image processing apparatus 100 according to the embodiment. The tracking display of a region of interest is an act of displaying, on an image yet to undergo non-linear alignment, such a region of interest on a target image that matches a region of interest set on a reference image. Image A on the upper left of FIG. 12 is an image acquired by first imaging. Image B on the upper right of FIG. 12, which is acquired by second imaging, is an image yet to undergo non-linear alignment. In FIG. 12, the region of interest set on image A is shown as a region of interest T14 and the region of interest set on image B at same coordinates as the region of interest T14 is shown as a region of interest T15B.

On the other hand, the region of interest on image B located at a same position as the region of interest T14 after non-linear alignment is shown as a region of interest T15A. As shown in image B of FIG. 12, the region of interest T15A after the non-linear alignment is deformed compared to the region of interest T15B. In this way, the region of interest resulting from the alignment may be displayed on image B yet to undergo alignment, showing how the region of interest has moved as a result of the alignment.

Also, the lower part of FIG. 12 shows a TDC. As indicated by a broken line and a solid line, respectively, in the lower part of FIG. 12, a TDC before application of non-linear alignment and the above-mentioned CT value correction and a TDC after alignment and CT value correction may be displayed together. From among the region of interest T15A and region of interest T15B shown in the upper part of FIG. 12, a TDC corresponding to a region of interest selected by the user may be displayed.

While observing, on a display such as shown in FIG. 12, how the region of interest changes due to positional displacement among time phases, the user can analyze the TDC. That is, the user can check, on the image, what region the user is based on in creating the TDC, and thus it is easy for the user to conduct a comprehensive diagnosis taking both the image and TDC into consideration.

Note that whereas in the above embodiment, CT images acquired by dynamic imaging on an X-ray CT apparatus have been described as an example, the technical idea of the above embodiment is not limited to CT images, and is similarly applicable to X-ray images acquired by other medical image diagnostic apparatuses, such as an X-ray angiography apparatus, which use X-rays. Also, in imaging with an MRI (Magnetic Resonance Imaging) apparatus, changes in the densities of the substances contained in a tissue affect signal strength. Therefore, with an MRI apparatus, pixel values can be corrected by finding deformation rates using a method similar to the one described in the above embodiment.

Also, the above embodiment has been described by taking the medical image processing apparatus 100 as an example, but this is only an example. The correction of pixel values in the above embodiment is applicable to other medical image diagnostic apparatuses such as an X-ray CT apparatus. An embodiment of the medical image diagnostic apparatus will be described by taking an X-ray CT apparatus as an example.

Figure 13:
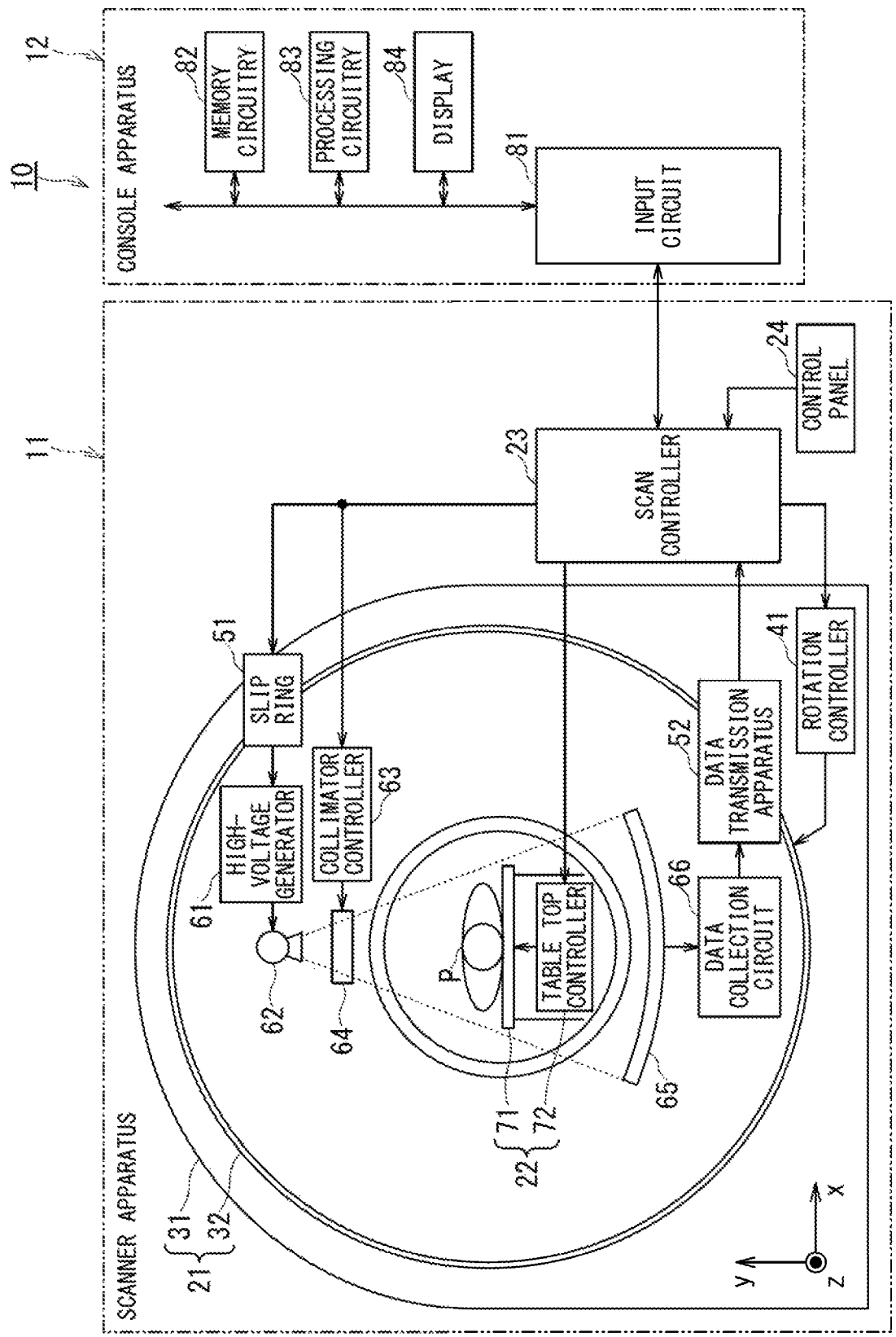
FIG. 13 is a conceptual configuration diagram showing an example of the X-ray CT apparatus according to the embodiment.

FIG. 13 is a conceptual configuration diagram showing an example of the X-ray CT apparatus according to the embodiment. The X-ray CT apparatus in FIG. 13 includes a scanner apparatus 11 and a console apparatus 12.

The scanner apparatus 11 is normally installed in an examination room and configured to generate, for example, X-ray transmission data on a subject P. On the other hand, the console apparatus 12 is normally installed in a control room next to the examination room and configured to generate projection data based on the transmission data and thereby generate and display a reconstructed image.

The scanner apparatus 11 includes a gantry apparatus 21, a bed apparatus 22, a scan controller 23, and a control panel 24.

The gantry apparatus 21 is also called a gantry and includes a fixed gantry 31 fixed to a non-illustrated foundation and a rotary gantry 32.

The fixed gantry 31 includes a rotation controller 41. The rotation controller 41 rotates the rotary gantry 32 relative to the fixed gantry 31 on instructions from the scan controller 23.

The fixed gantry 31 and rotary gantry 32 include a slip ring 51 and data transmission apparatus 52.

The slip ring 51 is a rotary connector adapted to secure electric conduction, while slipping, by laterally pressing brushes such as carbon brushes or wire brushes located on the side of the fixed gantry 31 against an annular electric circuit (metal ring) concentrically placed in the rotary gantry 32.

The data transmission apparatus 52 includes a transmitting circuit on the side of the rotary gantry 32 and a receiving circuit on the side of the fixed gantry 31. The transmitting circuit transmits raw data generated by a data collection circuit 66 described later to the receiving circuit on a non-contact basis. The receiving circuit supplies the raw data transmitted from the transmitting circuit to the scan controller 23 described later.

The rotary gantry 32 includes a high-voltage generator 61, an X-ray tube 62, a collimator controller 63, an X-ray optical system 64, an X-ray detector 65, and the data collection circuit 66. The rotary gantry 32 is also called a rotating frame. The rotary gantry 32 integrally holds the aftermentioned high-voltage generator 61, data collection circuit 66, and the like. That is, with the X-ray tube 62 and X-ray detector 65 opposed to each other, the rotary gantry 32 can rotate integrally around the subject P. As an example, a direction parallel to a rotation center axis of the rotary gantry 32 is defined herein as a z-axis direction and a vertical direction is defined as a y-axis direction.

Based on a control signal received from the scan controller 23 via the slip ring 51, the high-voltage generator 61 supplies electric power needed in order to perform a scan to the X-ray tube 62.

The X-ray tube 62 generates X-rays by bombarding a metal target with an electron beam at an X-ray tube voltage supplied from the high-voltage generator 61 and directs the X-rays onto the X-ray detector 65. An X-ray fan beam or X-ray cone beam is generated from the X-rays emitted from the X-ray tube 62. Electric power necessary for X-ray irradiation is supplied to the X-ray tube 62 under control of the scan controller 23.

Under the control of the scan controller 23, the collimator controller 63 adjusts an irradiation range of the X-rays in a slice direction of the X-ray optical system 64.

The X-ray optical system 64 includes various tools adapted to control irradiation conditions such as a dosage, the irradiation range, a shape, and radiation quality of the X-ray beam. Specifically, the X-ray optical system 64 includes a wedge filter and a collimator. The wedge filter adjusts an X-ray dosage of the X-rays generated by the X-ray tube 62. The collimator which operates under control of the collimator controller 63, is a slit adapted to narrow the X-ray irradiation range of the X-rays whose dosage has been adjusted.

The X-ray detector 65 is, for example, a one-dimensional array-type detector which has plural detecting elements in a channel direction and a single detecting element in a column (slice) direction. As another example, the X-ray detector 65 may be a two-dimensional array detector with, plural detecting elements arranged in a matrix, i.e., with plural detecting elements arranged both in the channel direction and slice direction. The X-ray detector 65 detects the X-rays emitted from the X-ray tube 62.

The two-dimensional array detector is also called a multi-slice detector. When the X-ray detector 65 is a multi-slice detector, a three-dimensional region having a width in a column direction can be scanned by a single rotation (or a half rotation+α) of the rotary gantry 32. This scan is referred to as a volume scan.

The data collection circuit 66 has plural DASs (data acquisition systems). The DASs collect data in synchronization with switching of the X-ray tube voltage during scanning. The DASs amplify signals of the transmission data detected by the respective detecting elements of the X-ray detector 65 and convert the amplified signals of the transmission data into raw data, which are digital signals. The DASs transmit projection data to the scan controller 23 via the data transmission apparatus 52.

The bed apparatus 22 of the scanner apparatus 11 includes a table top 71 and a table top controller 72. The table top 71 is configured to be able put the subject P thereon.

Under the control of the scan controller 23, the table top controller 72 moves the table top 71 up and down along a Y direction and moves the table top 71 on which the subject P is placed, horizontally along a Z direction as described below. That is, the table top controller 72 inserts the table top 71 toward an opening which includes a rotation center of the rotary gantry 32, and retracts the table top 71 through the opening when imaging is finished.

Note that in the case of an upright CT apparatus which images the subject P in a standing position or sitting position, the table top controller 72 controls a patient transfer mechanism corresponding to the table top 71 under the control of the scan controller 23.

The scan controller 23 includes a non-illustrated CPU (Central Processing Unit), memory, and the like. The scan controller 23 controls various components of the gantry apparatus 21, including the rotation controller 41, high-voltage generator 61, collimator controller 63 as well as the table top controller 72 of the bed apparatus 22 on commands inputted via the control panel 24 or console apparatus 12.

The control panels 24 are provided on both sides of or in front of and behind the opening of the gantry apparatus 21. An operator can enter various commands and conditions via the control panel 24 while checking a state of the subject P. Specifically, via the control panel 24, the operator enters directions to turn on and off a non-illustrated floodlight adapted to emit light used to visually check the X-ray irradiation range as well as commands to move, stop, and automatically feed the table top 71.

The console apparatus 12 of the X-ray CT apparatus 10 is configured based on a computer and is capable of intercommunicating with external apparatus via a network such as a LAN (Local Area Network). The console apparatus 12 is made up of basic hardware including processing circuitry 81, memory circuitry 82, an input circuit 83, and a display 84. The processing circuitry 81 is interconnected with each hardware component of the console apparatus 12 via a bus serving as a common signal transmission path. Note that the console apparatus 12 may be equipped with a storage media drive.

The console apparatus 12 of FIG. 13 takes care of various types of image processing, display, and the like and has functions equivalent to those of the medical image processing apparatus 100 described above. Therefore, the console apparatus 12 of the X-ray CT apparatus 10 can perform operations equivalent to those of the medical image processing apparatus 100 described in FIGS. 1 to 12.

Whereas the X-ray CT apparatus 10 has been described as an example in FIG. 13, when an MRI apparatus is used as a medical image diagnostic apparatus instead of the X-ray CT apparatus 10, the medical image diagnostic apparatus is equipped with an apparatus adapted to collect magnetic resonance signals instead of the scanner apparatus 11 adapted to collect medical images using X-rays. Also, when an X-ray angiography apparatus is used as a medical image diagnostic apparatus, the medical image diagnostic apparatus is equipped with a C arm or arm instead of the scanner apparatus 11.

The medical image processing apparatus 100 according to at least one of the embodiments described above can correct pixel values of an image according to the deformation rate of an organ among time phases when the pixel values of the image changes with deformation of the organ.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus which analyzes blood flow dynamics in a predetermined region of a subject, the blood flow dynamics being generated from medical images obtained by imaging the predetermined region in time sequence over a plurality of time phases, the medical image processing apparatus comprising:
processing circuitry configured to
correct pixel values of a target image after being aligned, according to an amount of deformation of the target image when the target image is aligned with a reference image by executing the program read out from memory circuitry, the reference image and the target image being among the medical images in the plurality of time phases,
set a same grid on each of the reference image and the target image, thereby dividing each of the reference image and the target image into a plurality of regions in a grid-like arrangement,
calculate a relational expression between the deformation rate of the grid and a rate of change of the pixel values, and
correct the medical image based on the relational expression.

2. The medical image processing apparatus according to claim 1, wherein the processing circuitry is further configured to
calculate a deformation rate of the grid on the target image subjected to the alignment, by comparison with the grid on the reference image, and
multiply pixel values of a target image after being aligned by a reciprocal of the deformation rate of the grid and thereby correcting the pixel values of the target image after being aligned.

3. The medical image processing apparatus according to claim 1, wherein the processing circuitry is further configured to conduct image analysis based on the corrected medical image using a time density curve, generate an analysis result, and control a display to display the analysis result.

4. The medical image processing apparatus according to claim 2, wherein the processing circuitry is further configured to conduct image analysis based on the corrected medical image using a time density curve, generate an analysis result, and control a display to display the analysis result.

5. The medical image processing apparatus according to claim 3, wherein in the target image after being aligned, the processing circuitry determines a region with a high rate of change to be an alert region, generates an alert display by superimposing the alert region on the medical image, and further presents the alert display on the display.

6. The medical image processing apparatus according to claim 4, wherein in the target image after being aligned, the processing circuitry determines a region with a high rate of change to be an alert region, generates an alert display by superimposing the alert region on the medical image, and further presents the alert display on the display.

7. The medical image processing apparatus according to claim 3, wherein
the display displays a region of a medical image yet to undergo the alignment and a region of a medical image resulting from the alignment, the regions corresponding to a same region in the medical images, and
based on which of the region before the alignment and the region after the alignment is selected, the processing circuitry controls the display to display an analysis result generated based on the medical image yet to undergo the alignment, followed by an analysis result generated based on a medical image obtained by making a correction after the alignment.

8. The medical image processing apparatus according to claim 4, wherein
the display displays a region of a medical image yet to undergo the alignment and a region of a medical image resulting from the alignment, the regions corresponding to a same region in the medical images, and
based on which of the region before the alignment and the region after the alignment is selected, the processing circuitry controls the display to display an analysis result generated based on the medical image yet to undergo the alignment, followed by an analysis result generated based on a medical image obtained by making a correction after the alignment.

9. The medical image processing apparatus according to claim 5, wherein
the display displays a region of a medical image yet to undergo the alignment and a region of a medical image resulting from the alignment, the regions corresponding to a same region in the medical images, and
based on which of the region before the alignment and the region after the alignment is selected, the processing circuitry controls the display to display an analysis result generated based on the medical image yet to undergo the alignment, followed by an analysis result generated based on a medical image obtained by making a correction after the alignment.

10. The medical image processing apparatus according to claim 6, wherein
the display displays a region of a medical image yet to undergo the alignment and a region of a medical image resulting from the alignment, the regions corresponding to a same region in the medical images, and
based on which of the region before the alignment and the region after the alignment is selected, the processing circuitry controls the display to display an analysis result generated based on the medical image yet to undergo the alignment, followed by an analysis result generated based on a medical image obtained by making a correction after the alignment.

11. The medical image processing apparatus according to claim 3, wherein the processing circuitry generates a time density curve as an analysis result by performing calculations using a non-linear least squares method which assigns weights based on magnitude of a deformation rate of the grid.

12. The medical image processing apparatus according to claim 11, wherein the processing circuitry conducts a blood flow dynamics analysis based on the time density curve and displays a result of the blood flow dynamics analysis on the display.

13. The medical image processing apparatus according to claim 1, wherein the processing circuitry is further configured to
store the relational expression into the memory circuitry, and
correct the medical image based on the relational expression stored in the memory circuitry.

14. The medical image processing apparatus according to claim 1, wherein the medical images are acquired over the plurality of time phases in a same respiratory cycle after administering a contrast medium to the subject.

15. A medical image diagnostic apparatus, comprising:
a scanner configured to acquire a plurality of medical images by imaging a predetermined region of a subject in time sequence; and
processing circuitry configured to
correct pixel values of a target image according to an amount of deformation of the target image when the target image is aligned with a reference image by executing a program read out from memory circuitry, the reference image and the target image being among the medical images in the plurality of time phases,
set a same grid on each of the reference image and the target image, thereby dividing each of the reference image and the target image into a plurality of regions in a grid-like arrangement,
calculate a relational expression between the deformation rate of the grid and a rate of change of the pixel values, and
correct the medical image based on the relational expression.

16. The medical image processing apparatus according to claim 1, wherein the processing circuitry compares the target image after being aligned with the reference image, thereby calculating a deformation rate of the target image with respect to the reference image by alignment as the amount of deformation.

* * * * *